United States Patent [19]

Allen

[11] Patent Number: 4,781,591
[45] Date of Patent: Nov. 1, 1988

[54] ENDOSTEAL IMPLANT AND METHOD FOR PERFORMING IMPLANTATION THEREOF

[76] Inventor: James P. Allen, 490 Thomas Cove, Rochester, N.Y. 14625

[21] Appl. No.: 34,661

[22] Filed: Apr. 6, 1987

[51] Int. Cl.$^4$ .......................... A61C 8/00; A61F 5/04; A61F 2/28

[52] U.S. Cl. .................................. 433/174; 128/82.1; 128/92 YF; 128/92 W; 128/92 VM; 128/419 F; 433/173; 623/16

[58] Field of Search ................. 433/173, 174; 623/16; 128/82.1, 419 F, 92 YF, 92 W, 92 YP, 92 VM, 92 YE

[56] References Cited

U.S. PATENT DOCUMENTS

| | | | |
|---|---|---|---|
| 2,494,229 | 1/1950 | Collison | 128/92 YF |
| 2,532,296 | 12/1950 | Giesen | 128/92 YF |
| 3,918,440 | 11/1975 | Kraus | 128/82.1 |
| 4,027,392 | 6/1977 | Sawyer et al. | 433/174 |

FOREIGN PATENT DOCUMENTS

WO/85/023-37   6/1985   World Int. Prop. O. .......... 433/174

*Primary Examiner*—Ronald L. Frinks
*Attorney, Agent, or Firm*—Lawrence P. Kessler

[57] ABSTRACT

An endosteal implant, and the method for performing the implantation thereof, which promotes rapid and complete securing of the inplant to bone tissue. Soft tissure at a bone site is incised and a bore is drilled in the exposed bone. An implant housing is inserted in the bore. The implant housing is constructed so as to be able to receive a selectively removable electrical power source therewithin. When the power source is received within the housing located in the bore in the bone, and the soft tissue is sealed over the implant housing site, the power source produces an electrical current travelling through the tissue and the bone surrounding the site. Such current promotes cellular adhesion activity thereby substantially reducing the time for securing the implant housing to the bone. Subsequently, the electrical power source may be removed and replaced with a suitable abutment for affixing a desired prosthesis to the implant housing. Alternatively, the power source may be permanently left within the implant housing.

4 Claims, 2 Drawing Sheets 4,781,591

ENDOSTEAL IMPLANT AND METHOD FOR PERFORMING IMPLANTATION THEREOF

BACKGROUND OF THE INVENTION

This invention relates in general to endosteal implants, and more particularly to an endosteal implant, and the method for performing the implantation thereof, which promotes rapid and complete securing of the implant to bone tissue.

Endosteal implants are commonly used in the fields of dentistry and orthopedics, for example. In dentistry, the implants are typically used as bases for artificial dentures or supports for bridge work; while in orthopedics, they are used in artificial joint replacement or reduction of severe fractures. The implants are made from a material which is not subject to adverse chemical reaction within the implant site. For example, the implant material may be a metal such as titanium, an alloy of titanium, or an alloy of steel or chrome.

The implant, no matter what the material, must be treated to assure proper securing to the bone tissue so as to be capable of functioning according to its particular end purpose. With titanium implants, these implants are subjected to glow discharge cleaning. Glow discharge cleaning not only removes impurities from the surface of the implant, but also imparts a charge thereto. This surface charge improves cellular adhesion of the surrounding bone tissue to the implant. The improved cellular adhesion is primarily a result of reduced critical surface tension which enables a high degree of spreading and surface wetting by the body fluids surrounding the implant site over the implant. The body fluids promote formation of titanium oxide at the bone tissue/implant interface which effects securing of the implant to the bone tissue. However, even with the improved cellular adhesion provided by glow discharge cleaned titanium implants, the time required for adequate securing of implant to the bone tissue is in excess of six months.

SUMMARY OF THE INVENTION

This invention is directed to an endosteal implant, and the method for performing the implantation thereof, which promotes rapid and complete securing of the implant to bone tissue. Soft tissue at a bone site is incised and a bore is drilled in the exposed bone. An implant housing is inserted in the bore. The implant housing is constructed so as to be able to receive a selectively removable electrical power source therewithin. When the power source is received within the housing located in the bore in the bone, and the soft tissue is sealed over the implant housing site, the power source produces an electrical current traveling through the tissue and the bone surrounding the site. Such current promotes cellular adhesion activity thereby substantially reducing the time for securing the implant housing to the bone. Subsequently, the electrical power source may be removed and replaced with suitable abutment for affixing a desired prosthesis to the implant housing. Alternatively, the power source may be permanently left within the implant housing.

The invention, and its objects and advantages, will become more apparent in the detailed description of the preferred embodiment presented below.

BRIEF DESCRIPTION OF THE DRAWINGS

In the detailed description of the preferred embodiment of the invention presented below, reference is made to the accompanying drawings, in which.

DESCRIPTION OF THE PREFERRED EMBODIEMENT

Figure 1:
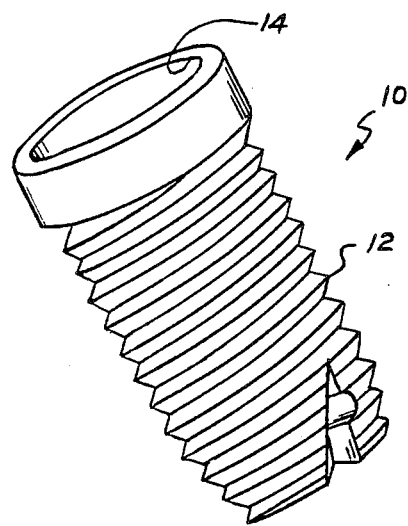
FIG. 1 is a view, in perspective, of the endosteal implant housing for use according to this invention.
Figure 2:
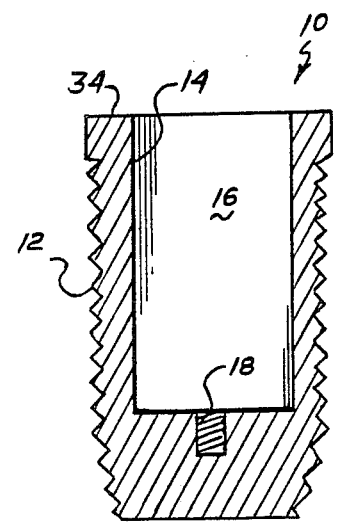
FIG. 2 is a side elevational view, in cross-section, of the endosteal implant housing of FIG. 1.

Referring now to the accompanying drawings, FIG. 1 shows an endosteal implant housing, designated generally by the numeral 10, for use with this invention. The implant housing 10 includes an externally threaded body 12 having a self-tapping feature. Preferably the housing is formed of titanium and is subjected to glow discharge cleaning in order to remove any impurities therefrom. Of course, the housing can be formed of an alloy of titanium, or an alloy of steel or chrome. Further, glow discharge cleaning imparts a surface charge to the housing which reduces critical surface tension to enable a high degree of spreading and surface wetting by body fluids surrounding an implant site over the implant to improve cellular adhesion.

Figure 3:
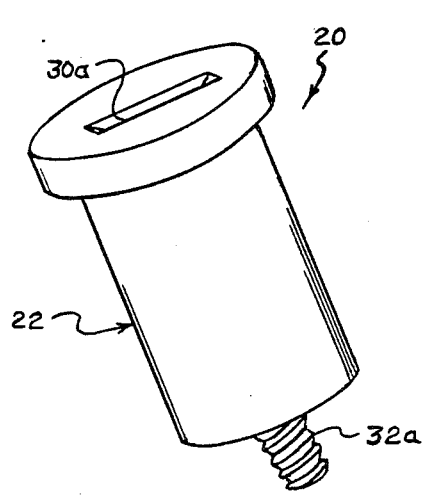
FIG. 3 is a view, in perspective, of a removable electrical power source for use with the endosteal implant housing of FIG. 1.
Figure 4:
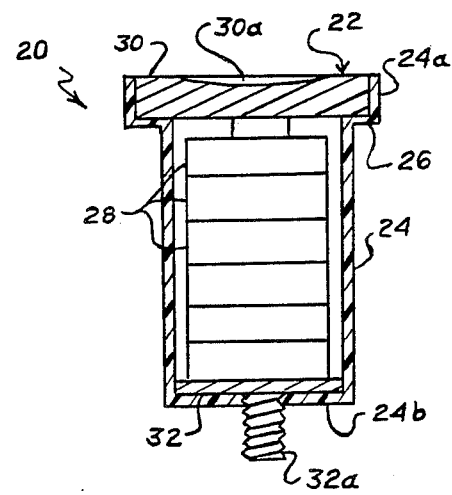
FIG. 4 is a side elevational view, partly in cross-section, of the electrical power source of FIG. 3.
Figure 8:
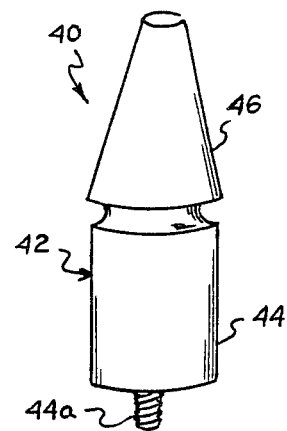
FIG. 8 is a view, in perspective, of a prosthetic-supporting abutment for the implant housing of FIG. 1.

The body 12 has an internal bore 14 forming a chamber 16. A threaded socket 18 is located at the base of the bore 14 and communicates with the chamber 16. The chamber 16 is adapted to selectively receive a self-contained electrical power source 20 (best shown in FIGS. 3 and 4) or a prosthesis affixing abutment 40 (best shown in FIG. 8).

The self-contained electrical power source 20 is, for example, any well known dry primary battery, with the only particular qualification being as to its size. An exemplary battery 22 shown in FIGS. 3 and 4, includes an insulated jacket 24 which has an external circumferential dimension substantially equal to the circumferential dimension of the bore 14 and a circumferentially enlarged head portion 24a forming a seating lip 26. The distance between the lip 26 and the the base 24b of the jacket 24 is substantially equal to the depth of the bore 14. A plurality of cells 28 (e.g., alkaline or mercury cells) are located within the jacket 24 and have terminals 30 and 32 respectively disposed in contact with the upper and lower cells. The cells are connected together in series and oriented such that the terminal 30 forms the anode, or negative terminal of the battery, and the terminal 32 forms the cathode, or positive terminal of the battery. The terminal 30 has a slot 30a formed therein adapted to receive the head of a screw driver for example; and the terminal 32 has an externally threaded post 32a adapted to mate with the threaded socket 18 of the implant housing.

Accordingly, the battery 22 can be removably secured within the chamber 16 of the implant housing 10 by screwing the post 32a into the socket 18 until the lip 26 seats on the top surface 34 of the housing. When secured in the implant housing 10, the battery 22 will produce a desired electrical current flow to promote cellular adhesion activity as described hereinbelow. Of course, other self-contained electrical power sources producing the desired electrical current flow are suitable for use with this invention. Such power sources may have finite life cycles or may be programmable to provide a controlled current flow of a desired duration or intensity.

The abutment 40 is, for example, a dental prosthesis supporting insert 42. The insert 42 comprises a base 44 and a fixture post 46. The base 44 has circumferential and axial dimensions substantially equal to the corresponding dimensions of the bore 14. An externally threaded post 44a is secured the base 44 and is adapted to mate with the threaded socket 18. The fixture post 46 is secured to the base 44 (or integrally formed therewith) at the opposite end from the post 44a. The fixture post is suitably configured to enable a desired dental prosthesis, such as a replacement tooth or bridge appliance, to be affixed thereto. Accordingly, the insert 42 can be removably secured within the chamber 16 of the implant housing 10 by screwing the post 44a into the socket 18. The fixture post 46 will then be properly located relative to the implant housing 10 for affixing of a desired prosthesis thereto. Of course it is contemplated that this invention may also be used in circumstances where the abutment is an orthopedic prosthetic insert or, in certain procedures, simply a plug-like insert for the bore 14 of the housing 10.

Figure 5:
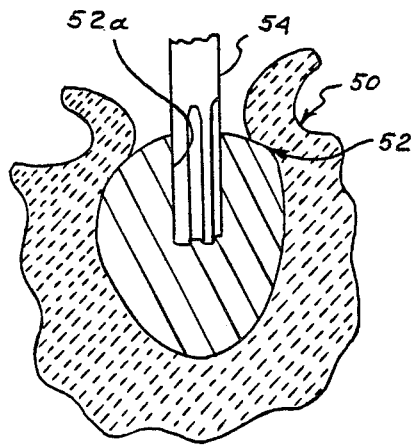
FIG. 5 is a side elevational view, partly in cross-section, of a typical site for implanting the implant housing of FIG. 1, depicting the preparation of such site for implant.
Figure 9:
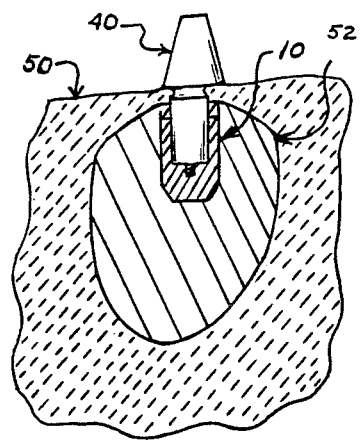
FIG. 9 is a view, similar to FIG. 5, depicting a completed implant for a dental prosthesis utilizing the implant housing of FIG. 1.
Figure 6:
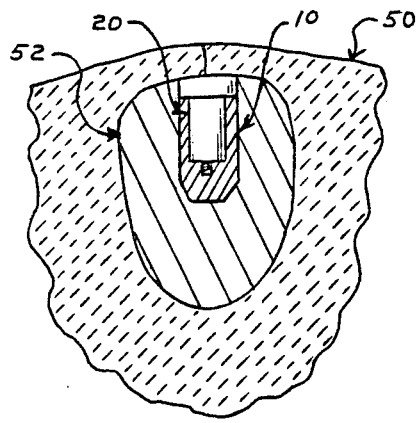
FIG. 6 is a view, similar to FIG. 5, depicting an inserted implant housing during the enhanced securing process.
Figure 7:
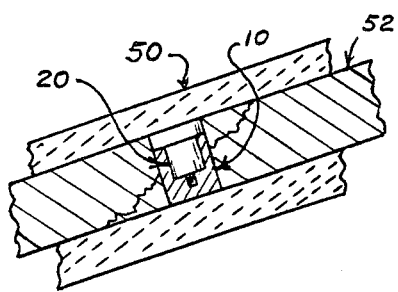
FIG. 7 is a view, similar to FIG. 6, depicting an inserted implant housing at an alternate site.

The procedure according to this invention for utilizing the endosteal implant which promotes rapid and complete securing of the implant to the bone tissue is described hereinbelow with reference to FIGS. 5, 6, and 9 as being for an implant in the posterior aleveolar process of the mandible. Of course it is understood that such procedure has many other dental and orthopedic applications which will subsequently become obvious to one of ordinary skill in the art (see for example FIG. 7 which shows the use of an implant according to this invention for reducing a bone fracture).

Partcularly, The soft tissue 50 over the desired implant site in the bone structure 52 is incised. A suitable bore 52a of the desired depth is then formed in the bone structure 52, such as by drilling with an internally and/or externally irrigated end cutting drill 54 (see FIG. 5). The implant housing 10 is then inserted into the bore 52a and, due to its self-tapping externally threaded body 12, will be retained in the bore. The self-contained electrical power source 20 is thereafter secured in the chamber of the implant housing 10, and the soft tissue 50 is sealed over the implant site, such as by suturing for example (see FIG. 6). The power source 20 will cause an electrical current flow through the soft tissue 50 and the bone structure surrounding the implant site. Such electrical current flow promotes substantially increased cellular adhesion thereby markedly reducing the time for complete securing of the implant housing 10 to the bone structure 52. For example, with the electrical current flow provided by the power source utilized in the procedure according to this invention, complete securing of the implant housing to the bone structure is typically accomplished in six to eight weeks, as compared to an excess of four to six months when using prior known procedures. Subsequently, the soft tissue 50, over the implant site, is incised and the power source is removed. An appropriate abutment 40 is then secured within the chamber 16 of the implant housing 10 and a desired prosthesis is affixed thereto to complete the procedure (see FIG. 9).

The invention has been described in detail with reference to a preferred embodiment thereof, but it will be understood that variations and modifications can be effected within the spirit and scope of the invention.

I claim:

1. An endosteal implant capable of substantially reducing the time for securing said implant to the bone, said implant comprising:
    an implant housing adapted to be placed at an endosteal site and covered with soft tissue, said housing defining a bore extending from one end of said housing interiorly thereof;
    a removable electrical power source selectively insertable into said bore of said housing and retainable therein to establish an electrical current flow through soft tissue and bone completely surrounding said housing when implanted at a desired endosteal site, whereby such current flow promotes cellular adhesion activity thereby substantially reducing the time for securing said implant to the bone, and
    an abutment selectively insertable in said bore of said housing for affixing a desired prosthesis to said housing when said power source is removed therefrom.

2. The invention of claim wherein said housing has an external configuration which makes said housing self-tapping.

3. The invention of claim 1 wherein said electrical power source is a dry primary battery.

4. A method for performing endosteal implant with a substantially reduced time for securing the implant to the bone, said method comprising the steps of:
    incising soft tissue to expose bone over the site where the implant is to be located;
    drilling a bore in the exposed bone;
    inserting in such bore, an implant housing having a removable power source;
    sealing the soft tissue over the implant housing using the electrical power source to produce an electrical current flow traveling through the soft tissue and bone surrounding the implant housing site to promote cellular adhesion activity thereby substantially reducing the time for securing the implant housing to the bone;
    incising the soft tissue over the site of the implant housing;
    removing the electrical power source from the housing; and
    replacing the power source with a suitable abutment for affixing a desired prosthesis to said implant housing.

* * * * *